United States Patent

Delavier et al.

Patent Number: 5,804,097
Date of Patent: Sep. 8, 1998

[54] LIQUID-CRYSTALLINE COMPOUNDS

[75] Inventors: Paul Delavier, Ludwigshafen; Karl-Heinz Etzbach, Frankenthal; Andreas Johann Schmidt, Freinsheim; Karl Siemensmeyer, Frankenthal; Gerhard Wagenblast, Wachenheim, all of Germany

[73] Assignee: BASF Aktiengesellschaft, Ludwigshafen, Germany

[21] Appl. No.: 648,134

[22] PCT Filed: Sep. 14, 1994

[86] PCT No.: PCT/EP94/03069

§ 371 Date: Aug. 22, 1996

§ 102(e) Date: Aug. 22, 1996

[87] PCT Pub. No.: WO95/08604

PCT Pub. Date: Mar. 30, 1995

[30] Foreign Application Priority Data

Sep. 25, 1993 [DE] Germany .......................... 43 32 733.8

[51] Int. Cl.$^6$ .......................... C09K 19/34; C09K 19/52; C09K 19/30; C09K 19/20
[52] U.S. Cl. .............. 252/299.63; 252/299.01; 252/299.61; 252/299.64; 252/299.65; 252/299.66; 252/299.67
[58] Field of Search .............. 252/299.01, 299.61, 252/299.63, 299.64, 299.65, 299.66, 299.67

[56] References Cited

U.S. PATENT DOCUMENTS 5,417,882  5/1995  Bach et al. .......................... 252/299.01

FOREIGN PATENT DOCUMENTS

| 37 03 640 | 9/1987 | Germany . |
| 38 30 968 | 4/1989 | Germany . |
| 38 27 603 | 3/1990 | Germany . |
| 40 11 812 | 10/1991 | Germany . |

OTHER PUBLICATIONS

Japanese Journal of Applied Physics, vol. 22, No. 10, pp. L661–L663, Oct. 1983, K. Miyasato, et al., "Direct Method with Triangular Waves for Measuring Spontaneous Polarization in Ferroelectric Liquid Crystals".

*Primary Examiner*—Shean C. Wu
*Attorney, Agent, or Firm*—Oblon, Spivak, McClelland, Maier & Neustadt, P.C.

[57] ABSTRACT

Liquid-crystalline compounds of the formula I $$X(-Y-A-Y-M-Y-B)_n \qquad I,$$

where

X is an aromatic or aliphatic ring system, n is an integer from 2 to 6, each Y, independently of the others, is a direct bond, —COO—, —OCO—, —O—, —CONH— or —CON(R)—, where R is $C_1$— to $C_4$-alkyl, A is a spacer, M is a mesogenic group and B is a side chain, are particularly suitable for use in displays or for the production of light-reflecting coatings.

11 Claims, No Drawings

LIQUID-CRYSTALLINE COMPOUNDS

This application is 371 of PCT/EP/03069 filed Sep. 14, 1994.

A large number of liquid-crystalline compounds is known. However, these generally do not solidify in a glass-like manner. Defined compounds having liquid-crystalline properties which do solidify in a glass-like manner are described, for example, in DE-A 37 03 640, DE-A 38 27 603, DE-A 38 30 968 and EP-A-504 660. A common feature of the compounds described in the first three applications is that they readily crystallize even from the glass state, and the orientation in the frozen state is thus unstable. Any mixtures employed in the case of crystallization are also no longer stable, since the requirement of the molecules to build up mixed crystals is very much stronger in the crystal than the requirements for miscibility in an anisotropic fluid.

The compounds described in EP-A-504 660 form stable glasses. They have a high dipole moment parallel to the long axis of the molecules and form nematic or smectic A phases. The dipole moment along the long axis of the molecules means that these materials align parallel thereto in an electric field; they therefore do not have ferroelectric properties, and any helical superstructures present are unstable in the electric field.

Also known are liquid-crystalline systems which have a defined structure and in which mesogenic groups are bonded to a central unit via a spacer (for example DE-A-40 11 811). However, these materials do not solidify in a glass-like manner, but instead crystallize very readily due to their high symmetry. Furthermore, Liquid Crystals 11 (5) (1992), 779, describes ferroelectric liquid crystals which are bonded to a central unit via a spacer. These materials have mesogenic structures which are unstable to heat and also to weak acids or bases and to water.

Desirable compounds for use as liquid-crystalline ferroelectric materials would be those which have a phase behavior in which the phase sequence passed through on cooling is nematic, smectic A and smectic C. Furthermore, the materials should have high flow viscosities in order to prevent the display from being pressure-sensitive, and in particular should be stable to weak acid bases.

A further desired feature is good miscibility with other liquid-crystalline compounds.

It is an object of the present invention to provide, novel liquid-crystalline compounds which solidify in a glass-like manner and which have smectic and nematic phases, are insensitive to variations in temperature and pH and to water and have high flow viscosity.

We have found that this object is achieved by compounds of the formula I $$X(-Y-A-Y-M-Y-B)_n \qquad I,$$

where

X is an aromatic or aliphatic ring system, n is an integer from 2 to 6, each Y, independently of the others, is a direct bond, —COO—, —OCO—, —O—, —CONH— or —CON(R)—, where R is $C_1$— to $C_4$-alkyl, A is a spacer, M is a mesogenic group and B is a side chain.

X is preferably trisubstituted phenyl or cyclohexyl, where the substituents are in particular in the meta-position to one another.

Of the radicals Y, particular preference is given to —OCO—, —O— and —COO—.

Spacers which can be used are all groups known for this purpose; the spacers are usually linked to X via ester or ether groups or via a direct bond. The spacers generally have from 2 to 30, preferably 2 to 12, carbon atoms and can be interrupted in the chain, for example, by O, S, NH or $NCH_3$. Suitable substituents for the spacer chain are fluorine, chlorine, bromine, cyano, methyl and ethyl.

Examples of representative spacers are:

$(CH_2)_p$, $(CH_2CH_2O)_mCH_2CH_2$, $CH_2CH_2SCH_2CH_2$, $$CH_2CH_2NHCH_2CH_2, \quad CH_2CH_2\underset{|}{\overset{CH_3}{N}}-CH_2CH_2,$$

$$(CH_2\underset{|}{\overset{CH_3}{C}}HO)_mCH_2CH, \quad (CH_2)_6\underset{|}{\overset{CH_3}{C}}H, \quad \text{or} \quad CH_2CH_2\underset{|}{\overset{Cl}{C}}H$$

where m is from 1 to 3 and p is from 1 to 12.

M can be a known mesogenic group. Particularly suitable are radicals containing aromatic or heteroaromatic groups. In particular, the mesogenic radicals conform to the formula III $$(-T-Y^1)_r-T \qquad III,$$

where each T, independently of the others, is an aromatic or heteroaromatic radical, each $y^1$, independently of the others, is O, COO, OCO, $CH_2O$, $OCH_2$, CH=N, N=CH or a direct bond, and r is from 1 to 3.

r is preferably 1 or 2.

T is generally an aromatic carbocyclic or heterocyclic ring system, which may be substituted by fluorine, chlorine, bromine, cyano, hydroxyl or nitro, conforming, for example, to the following base structures:

Particularly preferred examples of mesogenic groups M are:

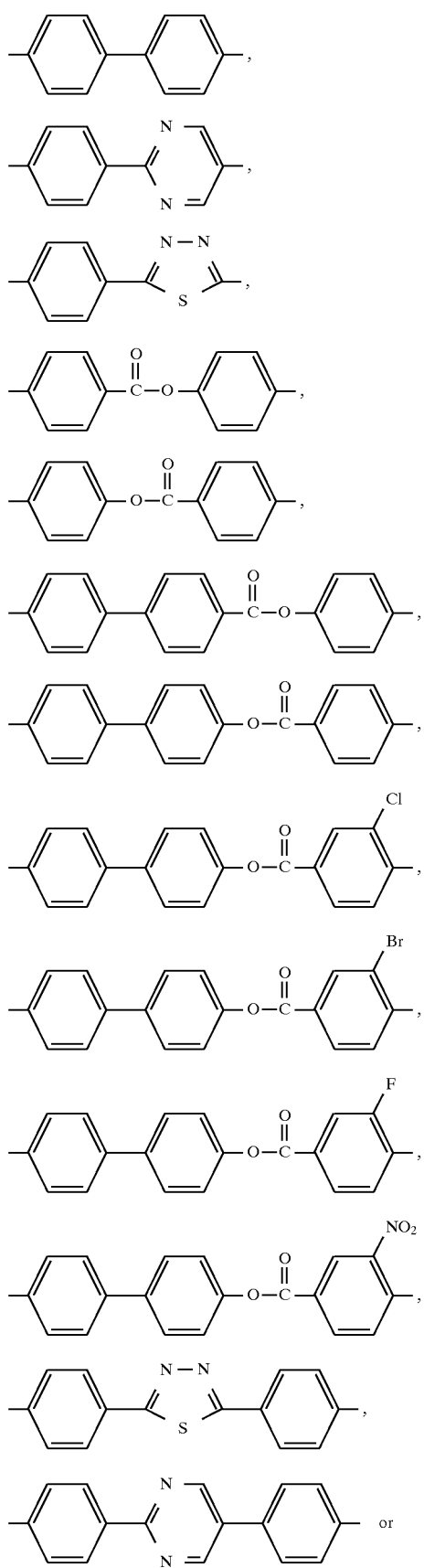

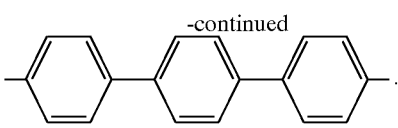

Examples of side chains B are $C_2$- to $C_{30}$-alkyl or -alkenyl, preferably $C_2$- to $C_{11}$-alkyl, where the radicals may be linear or branched, may be interrupted once or more than once by O, OCO, COO,

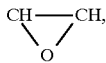

fluorine, chlorine, bromine, cyano or hydroxyl. Examples of individual radicals B are $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, $C_{11}H_{23}$, $C_{12}H_{25}$,

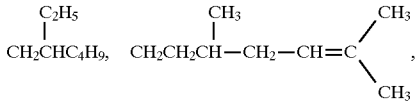

$CH_2CH=CH_2$, $(CH_2)_7CH=CH_2$ or $(CH_2)_8CH=CH_2$.
Examples of chiral side chains B are:

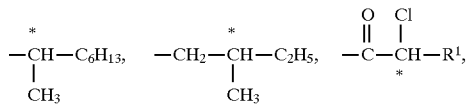

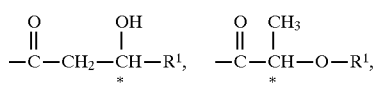

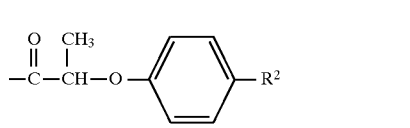

where $R^1$ is $C_1$- to $C_{12}$-alkyl, which may be chiral or achiral, and $R^2$ is $R^1$, fluorine or chlorine.
Examples of preferred radicals $R^1$ are:

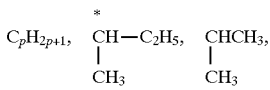

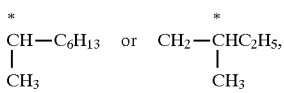

where p is from 1 to 12.

In order to prepare compounds of the formula I in which the Y adjacent to X is COO, CONH or

chlorides of the formula

can be reacted with a compound of the formula

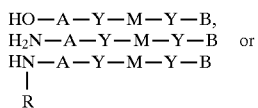

by methods known per se. For n=3 and the Y=adjacent to X OCO, compounds of the formula

can be reacted analogously with compounds of the formula

For Y=O, hydroxyl can be reacted with haloalkyl.

For compounds where n≠3, the corresponding applies, ie. general preparation methods are known from the literature; an example which may be mentioned is the reaction with dicyclohexylcarbodiimide (DCC) for the preparation of esters. Details on the reactions are given in the examples, in which parts and percentages are by weight, unless otherwise specified.

The compounds of the formula I are liquid-crystalline and, depending on the structure, can form smectic, nematic or cholesteric phases. They are suitable for all purposes for which liquid-crystalline compounds are usually used.

The novel compounds adopt a position between low-molecular-weight and polymeric liquid-crystalline compounds. In contrast to the polymers, they can be prepared reproducibly and have a substantially uniform structure, but nevertheless have viscosities like the polymers.

In order to obtain desired properties, it may be expedient to use mixtures of compounds of the formula I, it being possible for these mixtures to be prepared in situ or by mechanical mixing.

The novel compounds are particularly suitable for use in displays and for the production of light-reflecting coatings.

EXAMPLES

Some abbreviations used throughout the examples are shown below:
DCC dicyclohexylcarbodiimide
PP 4-pyrrolidinopyridine
DMAP 4-N,N-dimethylaminopyridine
C crystalline phase
Gl glass phase
I isotropic phase
S smectic phase
$S_C$ smectic C phase with ferroelectric arrangement of the mesogens
$S_A$ smectic A phase
$S_{Ca}$ smectic C phase with antiferroelectric arrangement of the mesogens
$S_x$ unclassified smectic phase
Ch cholesteric phase
N nematic phase
* chiral liquid-crystalline phases
Z central unit comprising the radicals X and Y The phase transition temperatures were recorded using a polarizing microscope. Temperature control was effected in a Mettler FP80/82 microscope heating stage. The spontaneous polarization was determined by the method of Miyasato et al., Jpn. J. Appl. Phys. 22 (1986), L230.

Example 1

Preparation of tris{6-[4-(4-pentoxyphenoxycarbonyl)phenoxy]hexyl} 1,3,5-benzenetricarboxylate a. Reaction of 4-benzoxybenzoic acid with thionyl chloride 4 mol of thionyl chloride and 0.2 ml of triethylamine are added to 1 mol of 4-benzoxybenzoic acid, and the mixture is heated to the boil until the evolution of gas is complete. The residual thionyl chloride is then removed by vacuum distillation, and the acid chloride is precipitated by addition of petroleum ether (boiling range 50° to 60° C.). The solid residue is dried at 40° C. under reduced pressure.

Yield: 23.6 g ≙ 96%.

b. Reaction of 4-benzoxybenzyl chloride with pentoxyphenol 0.1 mol of 4-benzoxybenzyl chloride is dissolved in 150 ml of toluene, the mixture is heated to the boil, and a solution of 0.11 mol of 4-pentoxyphenol, dissolved in a mixture of 50 ml of toluene and 0.2 mol of pyridine, is added dropwise over the course of 1 hour. The solution is refluxed for a further hour and then cooled, and the product is washed with water in order to remove the solvent and chromatographed on silica gel (toluene/ethyl acetate 5:1).

Yield: 32 g ≙ 82%.

c. Hydrogenation of 4-pentoxyphenyl 4-benzoxybenzoate 16.9 g (0.042 mol) of 4-pentoxyphenyl 4-benzoxybenzoate are introduced into 250 ml of ethanol and hydrogenated at room temperature using Raney nickel under a hydrogen atmosphere at atmospheric pressure. The catalyst is subsequently filtered off with suction and destroyed by means of ethanol. The filtrate is evaporated, and the product is purified by filtration through silica gel.

Yield: 10.93 g ≙ 83%.

Reaction of 4-pentoxyphenyl 4-hydroxybenzoate with 6-chloro-1-hexanol 0.07 mol of 4-pentoxyphenyl 4-hydroxybenzoate and 0.08 mol of 6-chloro-1-hexanol are dissolved in 250 ml of DMF. 0.15 mol of finely ground potassium carbonate is added to this solution, the reaction mixture is thermostatted at 80° C. The reaction is followed by thin-layer chromatography. When full conversion has been reached, the product is worked up by conventional methods and finally recrystallized from ethanol containing a trace of toluene.

Yield: 23.8 g ≙ 85%.

Reaction of 4-pentoxyphenyl 4-(6-hydroxyhexyloxy) benzoate with 1,3,5-benzenetricarbonyl trichloride 0.02 mol of 1,3,5-benzenetricarbonyl trichloride is dissolved in 150 ml of toluene, the mixture is heated to the boil, and a solution of 0.063 mol of 4-pentoxyphenyl 4-(6-hydroxyhexyloxy)benzoate, dissolved in a mixture of 50 ml of toluene and 0.2 mol of pyridine, is added dropwise in the course of 1 hour. The solution is refluxed for a further hour. When the reaction is complete, the mixture is evaporated to dryness and the product is purified by column chromatography (silica gel, toluene/ethyl acetate 3:1). The product is subsequently recrystallized from ethanol containing a trace of toluene.

Yield: 20.3 g ≙ 75%.

Phase transition temperatures:

Gl 35 $S_X$ 83 $S_A$ 87 N 108 I

The following are synthesized as described in Example 1:

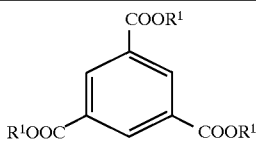

| Example | $R^1$ |
|---|---|
| 2 | $(CH_2)_6-O-$⟨⟩$-COO-$⟨⟩$-OC_6H_{13}$ |

C 96 ($S_A$ 91) N 111 I

| 3 | $(CH_2)_6-O-$⟨⟩$-COO-$⟨⟩$-OC_7H_{15}$ |

C 94 $S_A$ 95 N 109 I

| 4 | $(CH_2)_6-O-$⟨⟩$-COO-$⟨⟩$-OC_8H_{17}$ |

G1 35 $S_A$ 104 I

| 5 | $(CH_2)_6-O-$⟨⟩$-COO-$⟨⟩$-OC_{10}H_{21}$ |

C 70 $S_X$ 110 $S_A$ 117 I

| 6 | $(CH_2)_8-O-$⟨⟩$-COO-$⟨⟩$-OC_6H_{13}$ |

G1 31 $S_X$ 62 $S_A$ 46 N 103 I

| 7 | $(CH_2)_8-O-$⟨⟩$-COO-$⟨⟩$-OC_7H_{15}$ |

102 ($S_A$ 89.7 N 94.5) I

| 8 | $(CH_2)_8-O-$⟨⟩$-COO-$⟨⟩$-OC_{10}H_{21}$ |

C 108 ($S_A$ 102) I

Example 9

Reaction of 4-hexyloxyphenyl 4-(6-hydroxyhexyloxy) benzoate with 1,3,5-cyclohexanetricarbonyl trichloride 0.02 mol of 1,3,5-cyclohexanetricarbonyl trichloride is dissolved in 150 ml of toluene, the mixture is heated to the boil, and a solution of 0.063 mol of 4-hexyloxyphenyl 4-(6-hydroxyhexyloxy)benzoate, dissolved in a mixture of 50 ml of toluene and 0.2 mol of pyridine, is added dropwise over the course of 1 hour. The solution is refluxed for a further 1 hour. When the reaction is complete, the mixture is evaporated to dryness and the product is purified by column chromatography (silica gel, toluene/ethyl acetate 3:1). The product is subsequently recrystallized from ethanol containing a trace of toluene.

Yield: 19.8 g ≙ 72%.

Phase transition temperatures:

C 101 ($S_A$ 78 N 95) I

Examples 10 to 14 are synthesized as described for Example 9:

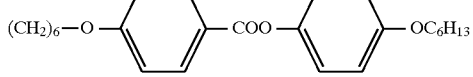

| Example | $R^1$ |
|---|---|
| 10 | $(CH_2)_6-O-$⟨⟩$-COO-$⟨⟩$-OC_7H_{15}$ |

G1 28 $S_X$ 72 $S_A$ 80 N 93 I

| 11 | $(CH_2)_6-O-$⟨⟩$-COO-$⟨⟩$-OC_{10}H_{21}$ |

G1 32 $S_X$ 70 $S_A$ 94 N 97 I

| 12 | $(CH_2)_8-O-$⟨⟩$-COO-$⟨⟩$-OC_6H_{13}$ |

C 100 ($S_A$ 95) I

| 13 | $(CH_2)_8-O-$⟨⟩$-COO-$⟨⟩$-OC_7H_{15}$ |

C 101 ($S_X$ 65 $S_A$ 87 N 91) I

| 14 | $(CH_2)_8-O-$⟨⟩$-COO-$⟨⟩$-OC_{10}H_{21}$ |

C 102 ($S_A$ 95) I

Example 15

Synthesis of a randomly mixed oligomesogen 0.02 mol of 1,3,5-cyclohexanetricarbonyl trichloride is dissolved in 150 ml of toluene, the mixture is heated to the boil, and a solution of 0.021 mol of 4-decyloxyphenyl 4-(6-hydroxyhexyloxy)benzoate, 0.021 mol of 4-decyloxyphenyl 4-(8-hydroxyoctyloxy)benzoate and 0.021 mol of 4-hexyloxyphenyl 4-(8-hydroxyoctyloxy) benzoate, dissolved in a mixture 50 ml of toluene and 0.2 mol of pyridine, is added dropwise over the course of 1 hour. The solution is refluxed for a further hour. When the reaction is complete, the mixture is evaporated to dryness and the product is purified by column chromatography (silica gel, toluene/ethyl acetate 3:1). The product is subsequently dried at 50° C. in a high vacuum.

The mixture prepared in this way theoretically contains ten different compounds distributed randomly with a very particular mass spectrum.

Yield: 22.6 g = 72%.

Masses ($M^+$) from time-of-flight mass spectroscopy (The $M^+$ values for the various species can be calculated from the various assignments possible on the basis of statistical laws: theoretical proportion of the mass of the whole=theoretical proportion.

The proportion of the mass determined in time-of-flight mass spectroscopy has been standardized to the $M^+$ peak at 1488 g/mol.)

| $M^+$/g/mol | 1488 | 1516 | 1544 | 1572 | 1600 | 1628 | 1656 |
|---|---|---|---|---|---|---|---|
| Proportion theoretical | 1 | 3 | 6 | 7 | 6 | 3 | 1 |
| Proportion found | 1 | 3.1 | 6 | 6.8 | 6 | 3.1 | 1 |

Phase transition temperatures:
Gl 23 $S_A$ 77 N 82 I

Example 16

Tris{11-[4-(4-heptylbenzoyl)phenoxy]undecyl} 1,3,5-benzenetricarboxylate a. Preparation of 4-benzoxyphenyl 4-heptylbenzoate 10.0 g (0.05 mol) of 4-benzoxyphenol are dissolved in 250 ml of absolute dichloromethane together with 11.0 g (0.05 mol) of 4-heptylbenzoic acid and 0.75 g (0.005 mol) of 4-pyrrolidinopyridine, and 15.4 g (0.075 mol) of DCC are added dropwise at from 0° to 5° C. After the mixture has been stirred at room temperature for 24 hours, the urea which has formed is filtered off with suction, the filtrate is evaporated, and the product is separated from the residue by column chromatography (silica gel, eluent toluene/ethyl acetate 5:1).

Yield: 16.9 g ≙ 84%.

b. Preparation of 4-hydroxyphenyl 4-methylbenzoate 16.9 g (0.042 mol) of 4-benzoxyphenyl 4-methylbenzoate are added to 250 ml of ethanol and hydrogenated at room temperature using Raney nickel under a hydrogen atmosphere at atmospheric pressure. The catalyst is subsequently filtered off with suction and destroyed using ethanol. The filtrate is evaporated, and the product is purified by filtration through silica gel.

Yield: 10.93 g ≙ 83%.

c. Preparation of 4-(11-hydroxyundecyloxy)phenyl 4-methylbenzoate 9.3 g (0.042 mol) of 4-hydroxyphenyl 4-methylbenzoate are dissolved in 80 ml of absolute dimethylformamide (DMF), and 6.8 g (0.05 mol) of potassium carbonate are added. 11.3 g (0.045 mol) of 11-bromo-1-undecanol are then added, and the mixture is heated at 80° C. for 24 hours. During this time, a further 0.6 g of potassium carbonate is added. For work-up, the reaction mixture is poured into ice water and acidified by means of dilute hydrochloric acid, and the precipitate is filtered off with suction. The residue is dissolved in ethyl acetate, washed with water, dried over sodium sulfate and freed from solvent under reduced pressure. The product is purified by column chromatography (silica gel, eluent toluene/ethyl acetate 5:1).

Yield: 6.54 g ≙ 39% d. Preparation of tris{11-[4-(methylbenzoyl)phenoxy]undecyl} 1,3,5-benzenetricarboxylate 0.82 g (0.003 mol) of 1,3,5-benzenetricarbonyl trichloride is dissolved in 215 ml of absolute toluene, and the solution is warmed to 100° C. At this temperature, a solution of 53 ml of absolute toluene, 1.07 g (0.013 mol) of pyridine and 3.7 g (0.0092 mol) of 4-(11-hydroxyundecyloxy)phenyl 4-methylbenzoate is added dropwise. The mixture is stirred at this temperature for 24 hours, allowed to cool and poured into 300 ml of ice water. 3 ml of concentrated hydrochloric acid are added, and the organic phase is separated off, washed a number of times with water, dried over sodium sulfate and freed from solvent under reduced pressure. The product is purified by column chromatography (silica gel, eluent toluene/ethyl acetate 5:1). After evaporation, the product is recrystallized from ethanol containing a trace of toluene.

Yield: 2.59 g ≙ 73%.
Phase behavior:
C 91 (S 54 N 76) I

Compounds 17 to 19 are prepared as described in Example 16:

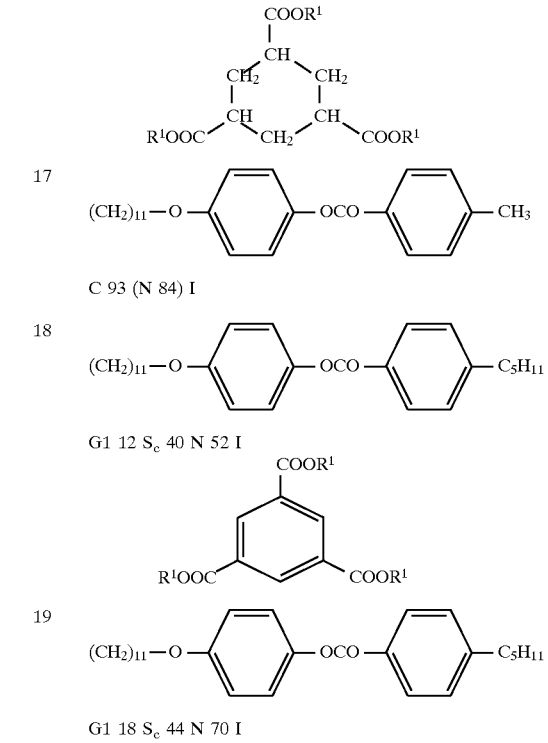

17  C 93 (N 84) I

18  Gl 12 $S_c$ 40 N 52 I

19  Gl 18 $S_c$ 44 N 70 I

Example 20

Reaction of 1,3,5-benzenetricarbonyl trichloride with ethyl 4-(3-hydroxypropoxy)-, 4-(6-hydroxyhexyloxy)- and 4-(8-hydroxyoctyloxy)biphenyl-4'-carboxylate 11.29 g (0.033 mol) of a mixture of ethyl 4-(3-hydroxypropoxy)-, 4-(6-hydroxyhexyloxy)- and 4-(8-hydroxyoctyloxy)biphenyl-4'-carboxylate, calculated as ethyl 4-(6-hydroxyhexyloxy)biphenyl-4'-carboxylate, are dissolved in 50 ml of absolute dichloromethane, and 2.65 g (0.01 mol) of 1,3,5-benzenetricarbonyl trichloride are added. 2.6 g (0.033 mol) of pyridine are added, and the reaction mixture is stirred overnight at room temperature. 5 ml of water and a little dilute hydrochloric acid are subsequently added, the organic phase is separated off, the solvent is removed by distillation, and the residue is dried.

Yield: 8.55 g.
Phase transition temperatures:
Gl 18 $S_A$ 133 I

Example 21 a. Chlorination of ethyl p-hydroxybenzoate 16.6 g (0.1 mol) of ethyl p-hydroxybenzoate are introduced into 50 ml of absolute dichloromethane, and 13.5 g (0.1 mol) of sulfuryl chloride are added. 7.5 g (0.1 mol) of diethyl ether are subsequently added dropwise. The temperature rises to 30° C., and vigorous evolution of HCl takes place. The mixture is stirred overnight. Since TLC analysis shows the presence of still unreacted starting material, a further 6.75 g (0.05 mol) of sulfuryl chloride are added. After 1 hour, the solid produced is filtered off with suction, washed with water until neutral and dried. The monochlorinated product is isolated by column chromatography (silica gel, eluent toluene/ethyl acetate 5:1).

Yield: 6.0 g ≙ 30%.

b. Etherification of ethyl 3-chloro-4-hydroxybenzoate using R-(−)-2-octanol 4.5 g (0.022 mol) of ethyl 3-chloro-4-hydroxybenzoate are dissolved in 35 ml of absolute tetrahydrofuran together with 2.9 g (0.022 mol) of R-(−)-2-octanol, and 8.7 g (0.033 mol) of triphenylphosphine are added. 5.6 ml (0.033 mol) of diethyl azodicarboxylate are slowly added dropwise at 0°–10° C. by means of a syringe. The reaction mixture is stirred at room temperature for 24 hours.

The mixture is subsequently evaporated on a rotary evaporator, and the residue is purified by column chromatography (silica gel, eluent toluene/ethyl acetate 5:1).

Yield: 5.38 g ≙ 78%.

c. Preparation of R-(−)-3-chloro-4-(2-octyloxy)benzoate 5.38 g (0.017 mol) of ethyl R-(−)-3-chloro-4-(2-octyloxy) benzoate are dissolved in 80 ml of ethanol, and 1.46 g (0.026 mol) of KOH are added. The mixture is refluxed for 3 hours; the solution is subsequently acidified using concentrated hydrochloric acid, ethyl acetate is added, and the precipitate is filtered off with suction. The residue is discarded, and the filtrate is evaporated to give the desired product.

Yield: 4.7 g ≙ 98%.

d. Reaction of 4-hydroxy-4'-(11-hydroxyundecanyloxy) biphenyl with 3,4-dihydropyran 42.72 g (0.12 mol) of 4-hydroxy-4'-(11-hydroxyundecanyloxy)biphenyl are dissolved in 200 ml of absolute chloroform, 10 drops of concentrated hydrochloric acid are added, 10.08 g (0.12 mol) of 3,4-dihydropyran are then added dropwise at 0°–5° C., and the mixture is slowly warmed to room temperature. After 2 hours, a further 5.0 g of 3,4-dihydropyran are added dropwise, and the mixture is warmed at 40° C. until starting material can no longer be detected. The reaction mixture is then extracted by shaking twice with NaCO₃ solution, and the organic phase is separated off and dried over Na₂CO₃. The solvent is removed by distillation, and the crude product is purified by column chromatography (silica gel, eluent toluene/ethyl acetate 5:1).

Yield: 27.1 g ≙ 51%.

e. Reaction of R-(−)-3-chloro-4-(2-octyloxy)benzoic acid with 4-hydroxy-4'-[1-(2-tetrahydropyranyl)undecanyloxy] biphenyl 4.4 g (0.01 mol) of R-(−)-3-chloro-4-(2-octyloxy)benzoic acid are dissolved in 80 ml of absolute dichloromethane together with 2.9 g (0.01 mol) of 4-hydroxy-4'-[1-(2-tetrahydropyranyl)undecanyloxy]biphenyl, and 0.15 g (0.001 mol) of 4-pyrrolidinopyridine is added. 3.08 g (0.015 mol) of dicyclohexylcarbodiimide, dissolved in 3 ml of absolute dichloromethane, are subsequently added dropwise at 0°–5° C., then the mixture is stirred at room temperature for 24 hours. The urea which forms is filtered off with suction, the filtrate is evaporated, and the desired product is purified by column chromatography (silica gel, eluent toluene/ethyl acetate 5:1).

Yield: 4.2 g ≙ 60%.

f. Removal of the tetrahydropyran protecting group 4.2 g (0.006 mol) of the compound prepared under e. are dissolved in 50 ml of absolute ethanol, three drops of concentrated hydrochloric acid are added, the mixture is stirred at 30° C. for about 18 hours. The product which precipitates is filtered off with suction and purified by column chromatography (silica gel, eluent toluene/ethyl acetate 5:1).

Yield: 1.7 g ≙ 46%.

g. Preparation of the oligomesogen from 1,3,5-benzenetricarbonyl trichloride and 4-(1-hydroxyundecanyloxy)biphenyl R-(−)-3-chloro-4-(2-octyloxy)benzoate The reaction and purification of the reaction products are carried out by a method similar to that described under Example 1.

Yield: 2.6 g ≙ 73%.

Phase behavior:

C 84 (Gl 35 $S_x$* 78) $S_c$* 104 Ch 109 I

Spontaneous polarization at T=90° C.: 105 nC cm$^{-2}$

Example 22

Preparation of the oligomesogen from 1,3,5-cyclohexanetricarbonyl trichloride and 4-(1-hydroxyundecanyloxy)biphenyl R-(−)-3-chloro-4-(2-octyloxy)benzoate The reaction is carried out by a method similar to that described under Example 8.

Yield: 2.4 g ≙ 70%.

Phase behavior:

C 90 (Gl 35 $S_X$ 84) $S_{ca}$* 104 I

Spontaneous polarization at T=90° C.: 90 nC cm$^{-2}$

The following compounds were synthesized as described under Examples 21 and 22:

| Example | R¹ |
|---------|----|
| 23 | 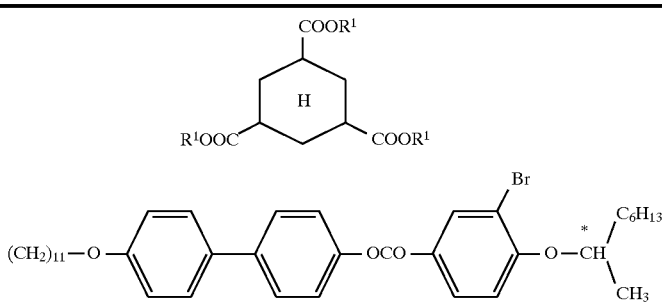 |

-continued

| Example | R¹ |
|---|---|

C 88 S$_{cA}$ 99 I

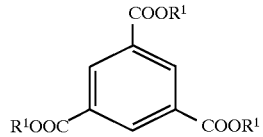

24

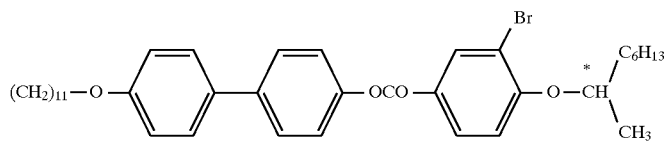

C 82 S$_c$* 95 I

25

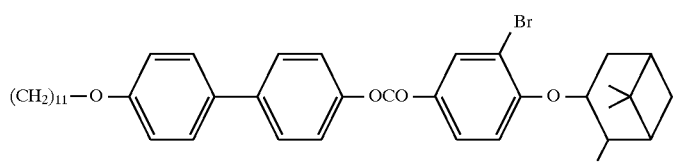

G1 32 S$_X$ 122 I

Example 26
a. Reaction of 4-hydroxybenzoic acid with acetic anhydride
153 g (1.5 mol) of acetic anhydride are dissolved in 150 ml of glacial acetic acid, and 138.0 g (1.0 mol) of 4-hydroxybenzoic acid and 10 drops of concentrated sulfuric acid are added. The mixture warms to 59° C., and is refluxed for a further 2 hours.

After the mixture has cooled, a little glacial acetic acid is added, and the product is filtered off with suction, washed with a little glacial acetic acid and water and then dried.
Yield: 131.8 g = 73%.

b. Reaction of 4-carboxyphenyl acetate with thionyl chloride
130.5 g (0.73 mol) of 4-carboxyphenyl acetate are introduced into 172.6 g (1.45 mol) of thionyl chloride at room temperature, a further 86.3 g (0.73 mol) of thionyl chloride are added, and the mixture is refluxed for 2 hours. The thionyl chloride is subsequently removed by distillation in a water-jet vacuum, and the residue is distilled in an oil-pump vacuum.
Yield: 128.8 g, b.p. 109°–112° C./2 mbar, 89%.

c. Reaction of ethyl octanoate with hydrazine hydrate
214.3 g (1.25 mol) of ethyl octanoate in 225 ml of ethanol are slowly added with vigorous stirring to 125.0 g (2.5 mol) of hydrazine hydrate in 170 ml of ethanol at reflux temperature. The residue formed is filtered off with suction and recrystallized from ethanol.
Yield: 143.4 g, m.p. 85°–86° C., 73%.

d. Reaction of octyl hydrazide with 4-actylbenzyl chloride
53.7 g (0.34 mol) of octyl hydrazide are introduced into 400 ml of absolute pyridine, and 67.4 g (0.34 mol) of molten 4-acetylbenzyl chloride are added with vigorous stirring at 10° C. The temperature rises to 30° C. The mixture is stirred at room temperature for a further 2 hours and poured onto 1.0 kg of ice, and the residue is filtered off with suction, washed with water and dried.
Yield: 112.1 g, 99%.

e. Ring closure to give 2-heptyl-5-(4-hydroxyphenyl)-1,3,5-thiadiazole
64.0 g (0.2 mol) of the product from d. are dissolved in 1.0 l of absolute toluene, and 96.0 g (0.26 mol) of Lawesson reagent are added. 20 ml of pyridine are added dropwise with vigorous stirring, and the mixture is refluxed for four hours. The mixture is evaporated on a rotary evaporator, the crude product is dissolved in 500 ml of pyridine, and 44.0 g (0.1 mol) of P$_4$S$_{10}$ are added. The mixture is stirred at 60° C. for two hours, and at 80° C. for a further four hours and then cooled, 50 ml of ethanol are added, and the mixture is poured onto 4.0 kg of ice. After the mixture has been stirred for one hour, the solid is filtered off with suction, washed with water and stirred with 600 ml of methanol, and 26.35 g (0.4 mol) of 85% strength KOH solution in 400 ml of methanol are added. The mixture is refluxed for 30 minutes, the solvent is then removed by distillation at atmospheric pressure, and the residue is dissolved in 600 ml of water, precipitated by means of concentrated hydrochloric acid, filtered off with suction, washed with water and dried.
Yield: 28.9 g, m.p. 72°–73° C., 52%.

f. Reaction of 2-heptyl-5-(4-hydroxyphenyl)-1,3,5-thiadiazole with 11-bromoundecanol
19.1 g (0.073 mol) of 2-heptyl-5-(4-hydroxyphenyl)-1,3, 5-thiadiazole are dissolved in 50 ml of absolute DMF, and 18.4 g (0.073 mol) of 11-bromoundecanol, 10.1 g (0.073 mol) of powdered potassium carbonate and 12.2 g (0.07 mol) of potassium iodide are added. After the mixture has been stirred at 80° C. for seven hours, a further 3.68 g (0.0124 mol) of 11-bromoundecanol, 2.0 g (0.0146 mol) of potassium carbonate and 2.44 g (0.0146 mol) of potassium iodide are added, and the mixture is again stirred at 80° C. for eight hours. The residue is filtered off with suction and washed with DMF, the organic phase is stirred with water, and the residue obtained is filtered off. After washing with water, the product is dried.
Yield: 25.6 g, m.p. 82°–83° C., 82%.

g. Reaction of 2-heptyl-5-[4-(11-hydroxyundecanyloxy) phenyl]-1,3,5-thiadiazole with 1,3,5-benzenetricarbonyl trichloride The reaction is carried out by a method similar to that described under Example 1.
Yield: 12.9 g = 28%.

Phase transition temperatures:

C 114 (S$_C$ 84 S$_A$ 99) I

Examples 27 to 29 are synthesized as described for Example 26.

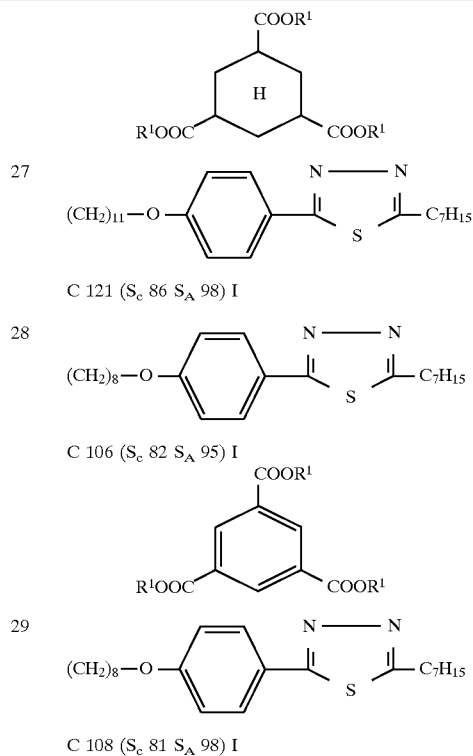

| Example | R$^1$ |
|---|---|
| 27 | C 121 (S$_c$ 86 S$_A$ 98) I |
| 28 | C 106 (S$_c$ 82 S$_A$ 95) I |
| 29 | C 108 (S$_c$ 81 S$_A$ 98) I |

Example 30 a. 2-(4-Hydroxyphenyl)-5-octylpyrimidine 137.7 ml (1.5 mol) of POCl$_3$ are added with ice cooling to 135 g (1.85 mol) of DMF, and the mixture is subsequently stirred at room temperature for 15 minutes. 202 g (1 mol) of decanal dimethyl acetal dissolved in 500 ml of DMF are then added dropwise, and, after addition is complete, the mixture is stirred for about 3 further hours. 262.5 g (1 mol) of 4-benzoxybenzamidine are subsequently added, and the mixture is stirred for a further hour. 1.1 l of triethylamine are then slowly added, during which the temperature rises to about 70° C. In order to maintain stirrability, about 700 ml of DMF are added, and the triethylamine is subsequently removed by distillation at atmospheric pressure. The residue is poured into about 6 l of ice water. The precipitated product is washed with water, recrystallized from 2.5 l of isobutanol, dissolved in 1 l of ethyl acetate and hydrogenated at atmospheric pressure with addition of 10 g of Pd/C (10%) until take-up of hydrogen ceases. The catalyst is filtered off with suction, and the residue from evaporation of the filtrate is dried at 50° C. under reduced pressure.

Yield: 130.3 g $\hat{=}$ 46%.

b. 8-[4-(5-Octylpyrimidin-2-yl)phenoxy]octan-1-ol 42.0 g (0.14 mol) of 2-(4-hydroxyphenyl)-5-octylpyrimidine are dissolved in 400 ml of DMF, and 38.7 g (0.28 mol) of K$_2$CO$_3$ and 36.0 g (0.21 mol) of 8-chlorooctan-1-ol are added. The mixture is subsequently heated at 100° C. with monitoring by TLC until the reaction is complete. The mixture is poured into 3 l of ice water, and the precipitated product is filtered off with suction, washed with water, dried under reduced pressure and recrystallized from cyclohexane.

Yield: 38.55 g $\hat{=}$ 67%.

C. Tris{8-[4-(5-octylpyrimidin-2-yl)phenoxy]octyl} 1,3,5-tricarboxylate

The reaction of 8-[4-(5-octylpyrimidin-2-yl)phenoxy]octan-1-ol with 1,3,5-benzenetricarbonyl trichloride is carried out by a method similar to that of Example 1.

Yield: 10.6 g $\hat{=}$ 76%.

Phase behavior:

C 91 (S$_A$ 90) I

Example 31

Tris{8-[4-(5-octylpyrimidin-2-yl)phenoxy]octyl} 1,3,5-cyclohexanetricarboxylate

The reaction of 8-[4-(5-octylpyrimidin-2-yl)phenoxy]octan-1-ol with 1,3,5-cyclohexanetricarboxylic acid is carried out by a method similar to that of Example 9.

Yield: 20.6 g $\hat{=}$ 74%.

Phase behavior:

C 78 (S$_A$ 75) I

The following compounds are synthesized by a method similar to that of Example 30 or 31

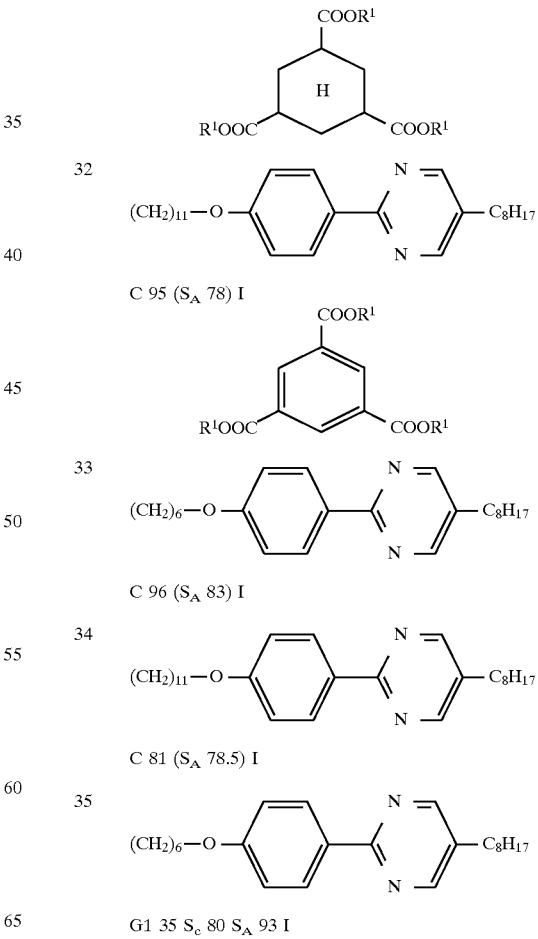

| Example | R$^1$ |
|---|---|
| 32 | C 95 (S$_A$ 78) I |
| 33 | C 96 (S$_A$ 83) I |
| 34 | C 81 (S$_A$ 78.5) I |
| 35 | G1 35 S$_c$ 80 S$_A$ 93 I |

| Example | R¹ |
|---|---|
| 36 | 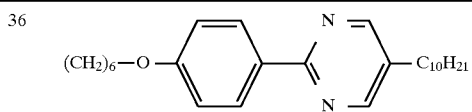<br>C 109 (S_c 79 S_A 95) I |
| 37 | 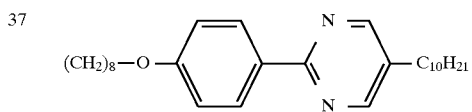<br>C 106 (S_A 92) I |
| 38 | 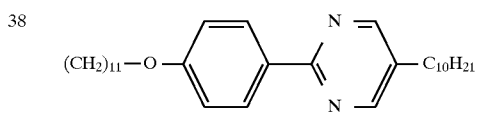<br>Gl 34 S_c 65 S_A 83 I |

Example 39

Synthesis of a mixed oligomesogen containing pyrimidine mesogens

The synthesis is carried out by a method similar to that described for Example 30, using 0.0024 mol of 1,3,5-benzenetricarbonyl trichloride, 0.0027 mol of 8-[4-(5-octylpyrimidin-2-yl) phenoxy]octan-1-ol, 0.0027 mol of 8-[4-(5-octylpyrimidin-2yl) phenoxy]hexan-1-ol and 0.0027 mol of 8-[4-(5-octylpyrimdin-2-yl)phenoxy]undecan-1-ol.

Yield: 2.6 g ≙ 70%.

Phase behavior:

Gl <25 S_A 71–82 I

The compounds of Examples 40 to 42 were synthesized by a method similar to that in Example 39. Examples 41 and 42 contain a decyl side chain.

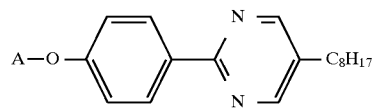

| Example | R¹ |
|---|---|
| 40 | mixture of<br>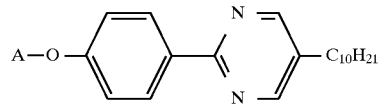<br>where A = (CH₂)₆, (CH₂)₈ and (CH₂)₁₁<br>Gl <20 S_A 70 I |
| 41 | mixture of<br><br>where A = (CH₂)₆, (CH₂)₈ and (CH₂)₁₁<br>Gl <20 S_A 74–84 I |
| 42 | as for Example 41, with trisubstituted phenyl as the central unit |

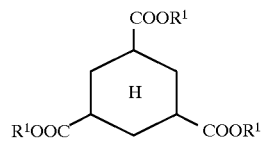

| Example | R¹ |
|---|---|
| | G1 <2 S_A 75–85 I |

Example 43

The synthesis of Example 43 is carried out by a method similar to that of Example 30.

a.) 4-(5-Octylpyrimidin-2-yl)phenyl 12-hydroxydodecanoate 0.034 mol of 2-(4-hydroxyphenyl)-5-octylpyrimidine, 0.051 mol of DCC and 0.1 g of DMAP are stirred for 24 hours at room temperature in CH₂Cl₂. The solvent is subsequently removed by distillation, and the residue is recrystallized from cyclohexane.

Yield: 12.65 g ≙ 77%.

b) Tris{11-[4-(5-octylpyrimidin-2-yl)phenoxycarbonyl]undecyl} 1,3,5-benzenetricarboxylate Method similar to that described under Example 30, using 0.005 mol of 1,3,5-benzenetricarbonyl trichloride and 0.015 mol of 4-(5-octylpyrimidin-2-yl)phenyl 12-hydroxydodecanoate.

Yield: 7.25 g ≙ 91%.

Phase transition temperatures:

Gl 28 S_C 56 S_A 72 I

Example 44

The synthesis of Example 44 is carried out by a method similar to that of Example 30.

a.) 2-(4-Hydroxyphenyl)-5-octanoxypyrimidine 0.1 mol of 4-benzoxybenzamidine and 0.1 mol of 2-octanoxyacetaldehyde dimethyl acetal are employed.

Yield: 2.8 g ≙ 9%.

b.) 8-[4-(5-Octanoxypyrimidin-2-yl)phenoxy]octan-1-ol 0.009 mol of 2-(4-hydroxyphenyl)-5-octanoxypyrimidine and 0.014 mol of 6-chlorooctan-1-ol are employed.

Yield: 3.96 g ≙ 99%.

c.) Tris{8-[4-(5-octanoxypyrimidin-2-yl)phenoxy]octyl} 1,3,5- benzenetricarboxylate 0.0025 mol of 1,3,5-benzenetricarbonyl trichloride and 0.0075 mol of 8-[4-(5-octanoxypyrimidin-2-yl)phenoxy]octan-1-ol are employed.

Yield after column chromatography on Al₂O₃ (eluent CH₂Cl₂):

0.5 g ≙ 14%.

Phase behavior:

Gl 86 S_A 114 I

Example 45

The synthesis of Example 45 is carried out by a method similar to that of Example 30.

a) 2-(4-hexyloxyphenyl)pyrimidin-5-ol 0.1 mol of 4-hexyloxybenzamidine and 0.1 mol of 2-benzoxyacetaldehyde dimethyl acetal are employed.

Yield: 3.7 g ≙ 14%.

b) 6-[2-(4-Hexyloxyphenyl)pyrimidin-5-yloxy]hexan-1-ol 0.013 mol of 2-(4-hexyloxyphenyl)-5-hydroxypyrimidine and 0.020 mol of 6-chlorohexan-1-ol are employed.

Yield: 5.0 g ≙ 97%.

c) Tris{6-[2-(4-hexyloxyphenyl)pyrimidin-5-yloxy]hexyl} 1,3,5-benzenetricarboxylate 0.003 mol of 1,3,5-benzenetricarbonyl trichloride and 0.01 mol of 6-[2-(4-hexyloxyphenyl)pyrimidin-5-yloxy] hexan-1-ol are employed.

Yield: 1.1 g ≙ 30%.

Phase transition temperatures:

C 36 $S_A$ 120 N 122 I

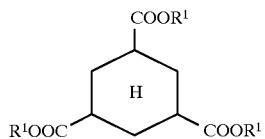

| Example | $R^1$ |
|---|---|
| 46 | 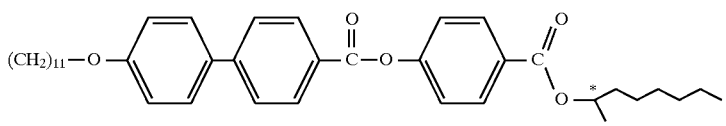 |

$S_{ca}^*$ 126 $S_A$ 130 I

| 47 | 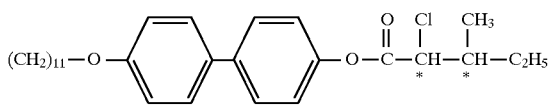 |

K 60 $S_A$ 97 I

| 48 | 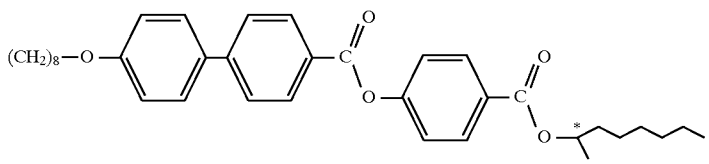 |

| 49 | 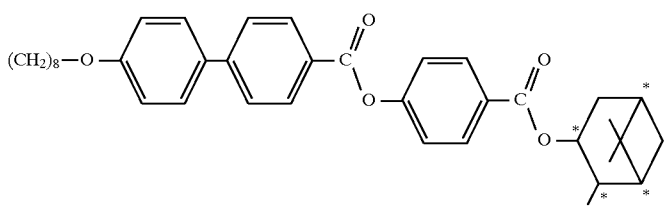 |

K 85 $S_c^*$ 150 $S_A$ 182 I
$P_s$ = 36.5 nC/cm²   T = 115° C.

| 50 | 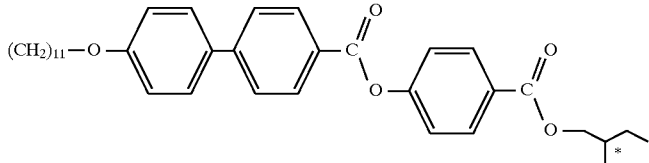 |

| 51 | 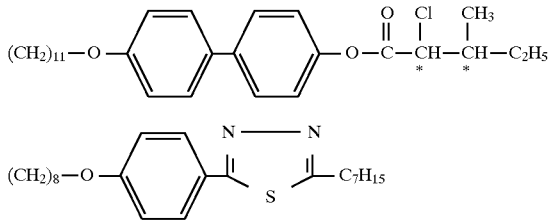 |

Ratio 1:2 (chiral:achiral) stated statistically
$S_c^*$ 57 $S_A$ 81 I
$P_s$ = 30 nC/cm²   T = 45° C.

-continued
52
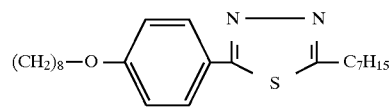
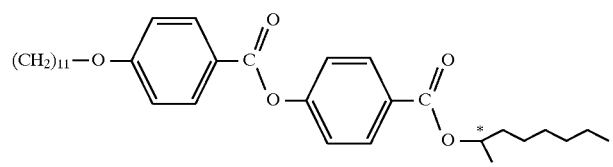
Ratio 1:1:1
$S_c^*$ 45 $S_A$ 60–67 I
53
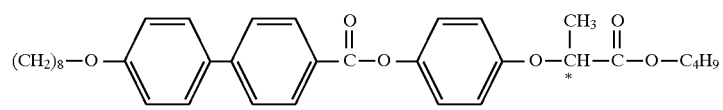
K 65 $S_c^*$ 100 $S_A$ 124 I
$P_s$ = 125 nC/cm$^2$   T = 80° C.
54
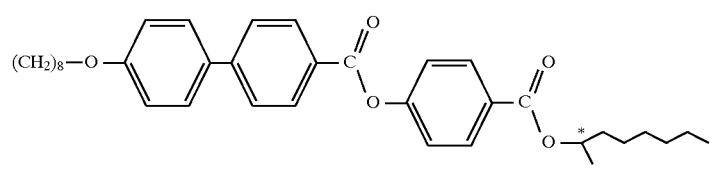
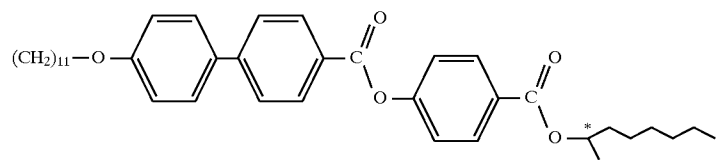
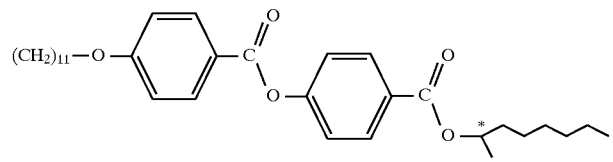
Ratio 1:1:1
$S_{ca}^*$ 93 $S_A$ 104–112 I
55
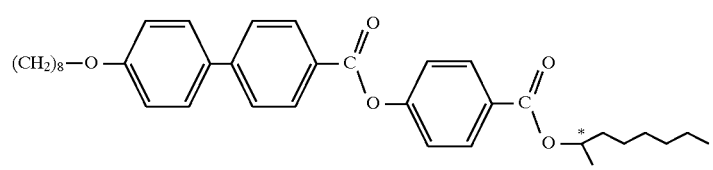
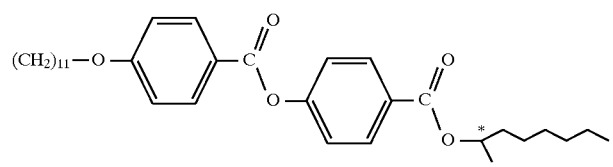
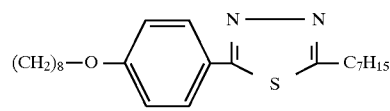

Ratio 1:1:1
$S_{ca}^* \, 82 \, S_A \, 90\text{--}95 \, I$
56 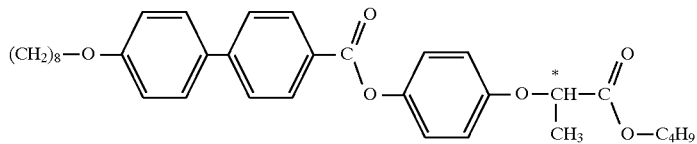
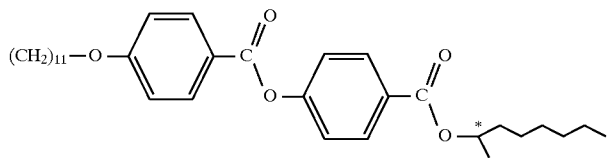
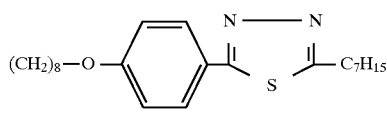
Ratio 1:1:1
57 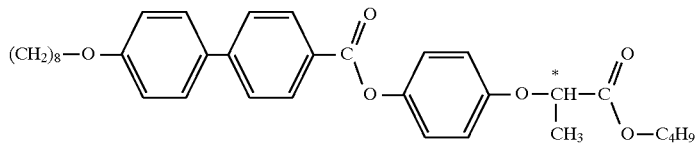
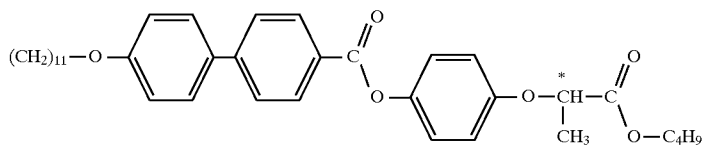
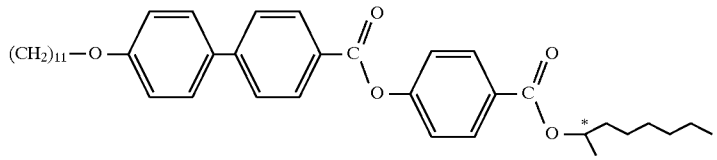
Ratio 1:1:1
56 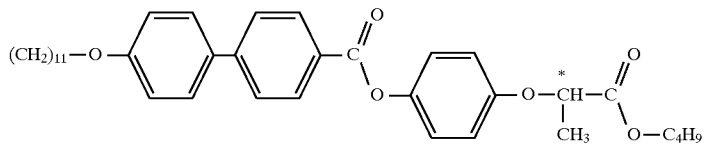
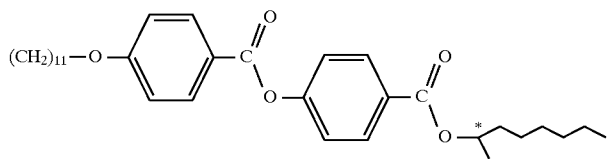
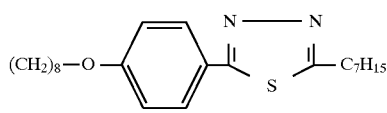
Ratio 1:1:1

|   |   | Proportions |
|---|---|---|
| 59 | | 0.75 |
| | | 0.75 |
| | | 0.75 |
| | | 0.75 |

$S_c$ 100 $S_A$ 127 I
$P_s$ (40° C.): 65 nC/cm² Θ (40° C.): 31.5°

| 60 | | 1 |
|---|---|---|
| | | 1 |
| | | 1 |

$S_c$ 65 $S_c/S_x/I$ 95 I
$P_s$ (40° C.): 115 nC/cm² Θ (40° C.): 23°

| 61 | | |
|---|---|---|

K 103 $S_c$ 110 $S_A$ 128 Ch 140 I

62 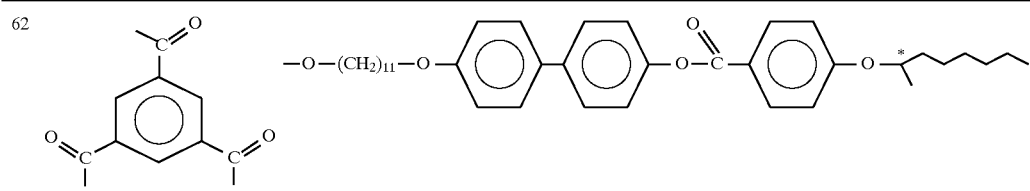
C$_n$ 105 S$_c$ 113 Ch 120 I
P$_s$ (110° C.): 25 nC/cm$^2$ Θ (110° C.): 20.5°
63 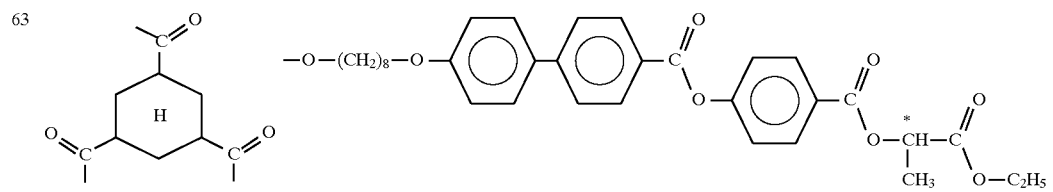
S$_c$ 60 S$_A$ 187 I
P$_s$ (70° C.): 178 nC/cm$^2$
64 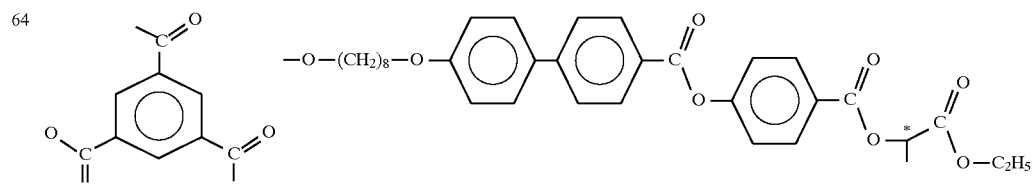
S$_x$ 70 S$_c$ 187 I
65 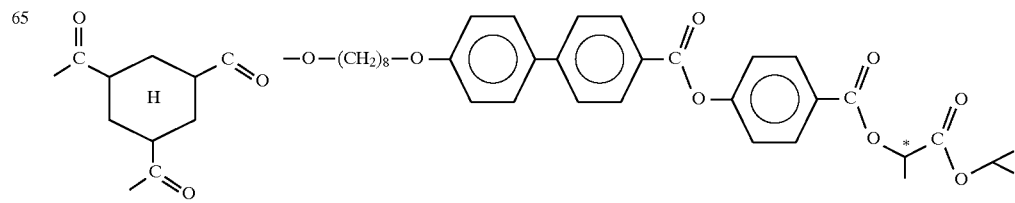
S$_x$ 50 S$_{ca}$* 176 I
66 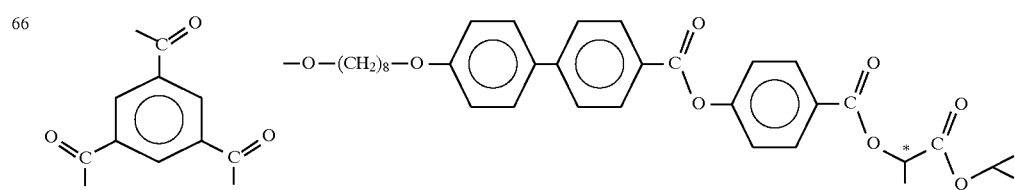
S$_c$ 70 S$_{ca}$* 178 I
67 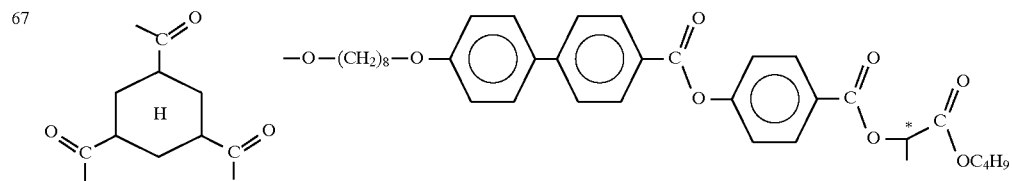
S$_x$ 40 S$_c$ 167 I

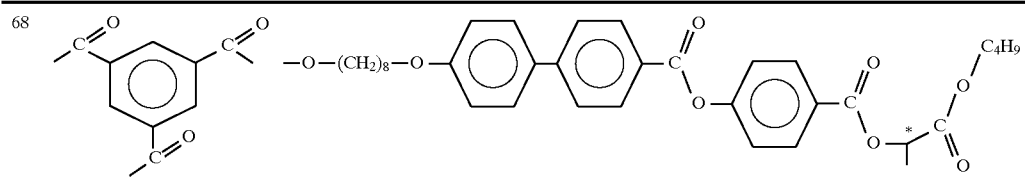
$S_x$ 65 $S_c$* 169 I
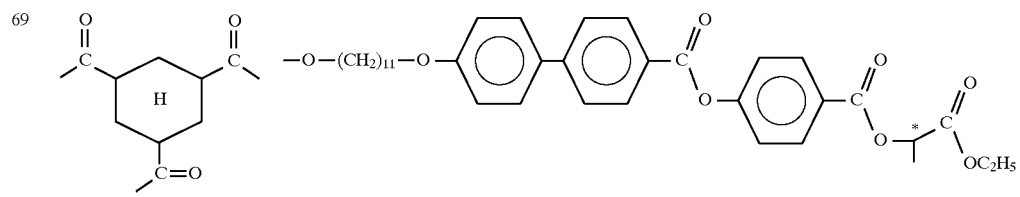
$S_x$ 40 $S_{ca}$* 177 I
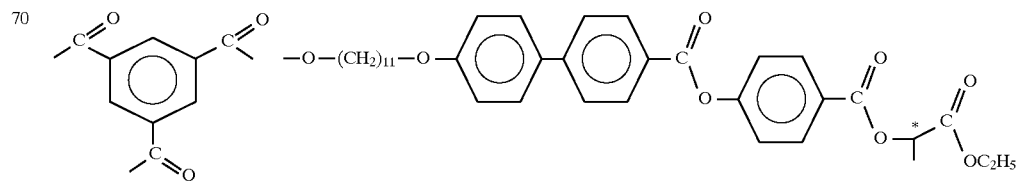
$S_{CA}$ 115 $S_C$ 145 $S_A$ 173 I
$P_s$ (130° C.): 60 nC/cm$^2$
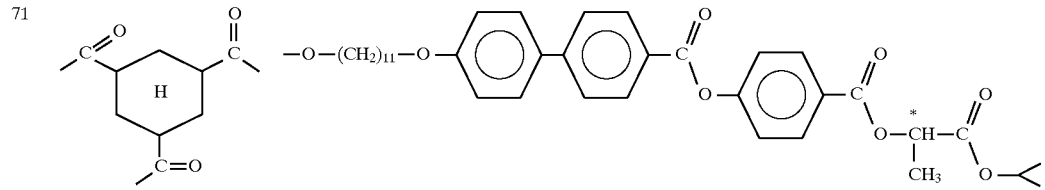
$S_x$ 138 $S_{ca}^{1}$* 145 $S_{ca}^{2}$* 165 I
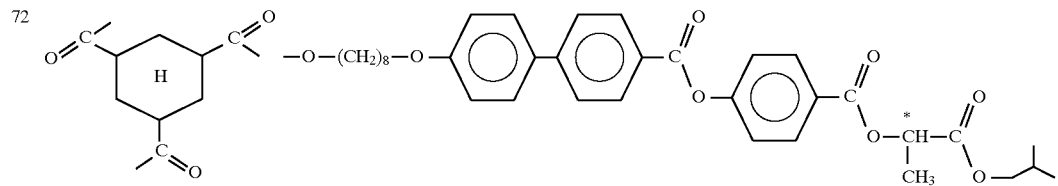
$S_{ca}$ 165 I
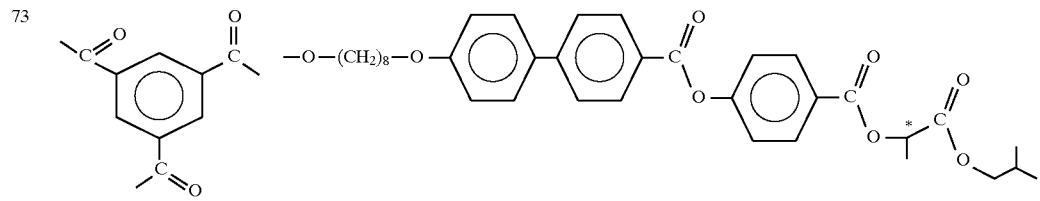
$S_c$ 169 I
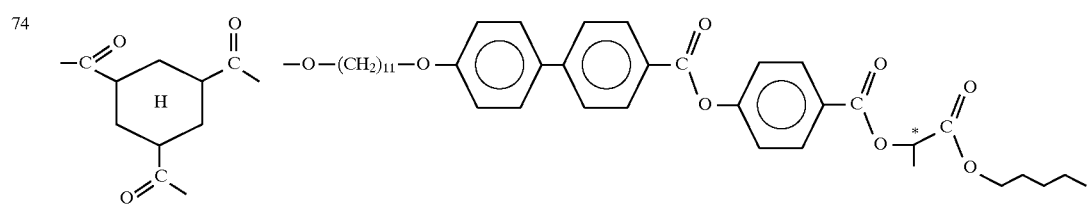

$S_x$ 40 $S_{ca}$ 144 $S_A$ 160 I
$P_s$ (135° C.): 12 nC/cm²
75 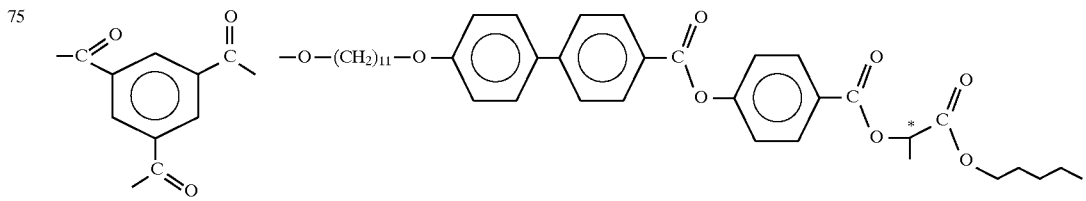
$S_x$ 43 $S_{ca}$ 81 $S_c$ 139 $S_A$ 159 I
76 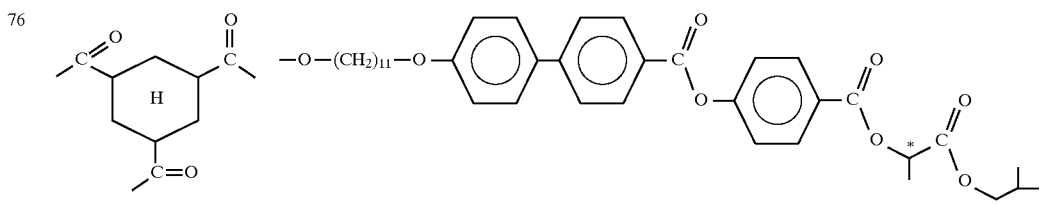
$S_x$ 40 $S_{ca}$ 145 $S_A$ 161 I
77 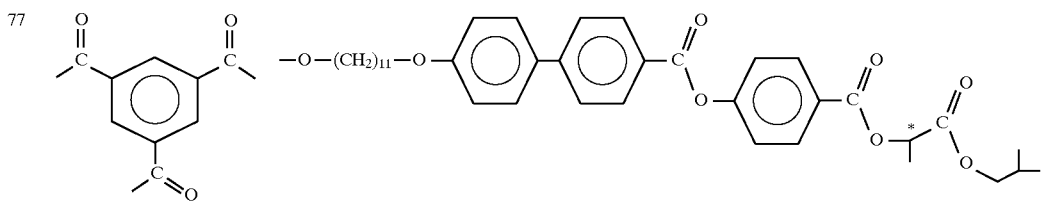
$S_x$ 85 $S_{ca}$ 110 $S_c$ 144 $S_A$ I
78 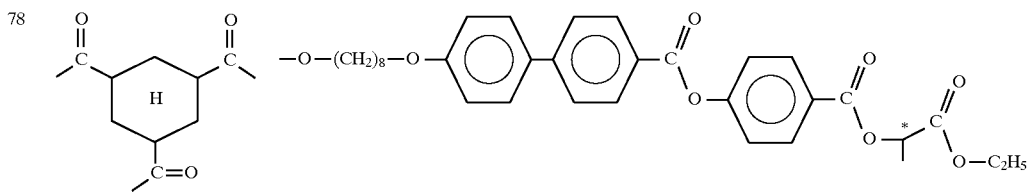 1
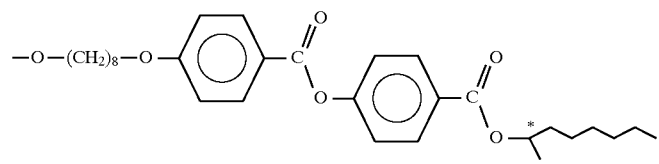 1
 0.5
 0.5
$S_x$ 40 $S_c$ 85 $S_A$ 110 I
$P_s$ (50° C.): 50 nC/cm²

| | | |
|---|---|---|
| 79 | [cyclohexane with three C(=O) groups, one H] | |
| | —O—(CH₂)₈—O—⟨⟩—⟨⟩—C(=O)—O—⟨⟩—C(=O)—O—*CH(CH₃)—C(=O)—O—C₂H₅ | 0.5 |
| | —O—(CH₂)₈—O—⟨⟩—⟨⟩—C(=O)—O—⟨⟩—C(=O)—O—*CH(CH₃)—C(=O)—O—C₄H₉ | 0.5 |
| | —O—(CH₂)₁₁—O—⟨⟩—C(=O)—O—⟨⟩—C(=O)—O—*CH(CH₃)—C₅H₁₁ | 1 |
| | —O—(CH₂)₈—O—⟨⟩—(thiadiazole)—C₇H₁₅ | 0.5 |
| | —O—(CH₂)₁₁—O—⟨⟩—(thiadiazole)—C₇H₁₅ | 0.5 |

$S_x$ 40 $S_c$ 70 $S_A$ 84–101 I
$P_s$ (50° C.): 110 nC/cm²

| | | |
|---|---|---|
| 80 | [cyclohexane with three C(=O) groups, one H] | |
| | —O—(CH₂)₈—O—⟨⟩—⟨⟩—C(=O)—O—⟨⟩—C(=O)—*CH(CH₃)—C(=O)—O—C₂H₅ | ⅔ |
| | —O—(CH₂)₈—O—⟨⟩—⟨⟩—C(=O)—O—⟨⟩—O—*CH(CH₃)—C(=O)—OC₄H₉ | ⅔ |
| | —O—(CH₂)₁₁—O—⟨⟩—C(=O)—O—⟨⟩—C(=O)—O—*CH(CH₃)—C₅H₁₁ | ⅔ |
| | —O—(CH₂)₈—O—⟨⟩—(thiadiazole)—C₇H₁₅ | 0.5 |
| | —O—(CH₂)₁₁—O—⟨⟩—(thiadiazole)—C₇H₁₅ | 0.5 |

$S_c$ 80 $S_A$ 116 I

-continued
| | | |
|---|---|---|
| 81 | 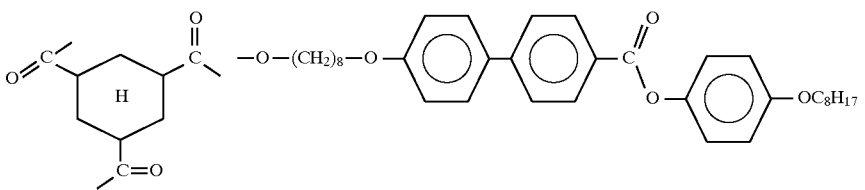 | |
| | —O—(CH₂)₈—O—⟨○⟩—⟨○⟩—C(=O)—O—⟨○⟩—OC₈H₁₇ | 0.5 |
| | —O—(CH₂)₁₁—O—⟨○⟩—⟨○⟩—C(=O)—O—⟨○⟩—OC₈H₁₇ | 0.5 |
| | —O—(CH₂)₈—O—⟨○⟩—⟨○⟩—C(=O)—O—⟨○⟩—O—*CH(CH₃)—C(=O)—O—C₄H₉ | 1.0 |
| | —O—(CH₂)₈—O—⟨○⟩—(N=N, S)—C₇H₁₅ | 0.5 |
| | —O—(CH₂)₁₁—O—⟨○⟩—(N=N, S)—C₇H₁₅ | 0.5 |
| | $S_x$ 40 $S_{ca}$ 85 $S_A$ 108 I | |
| 82 | 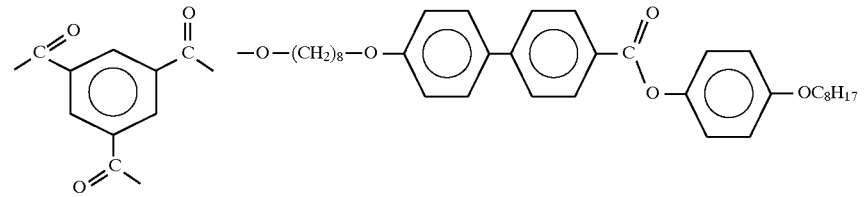 | |
| | —O—(CH₂)₈—O—⟨○⟩—⟨○⟩—C(=O)—O—⟨○⟩—OC₈H₁₇ | 0.5 |
| | —O—(CH₂)₁₁—O—⟨○⟩—⟨○⟩—C(=O)—O—⟨○⟩—OC₈H₁₇ | 0.5 |
| | —O—(CH₂)₈—O—⟨○⟩—⟨○⟩—C(=O)—O—⟨○⟩—O—*CH(CH₃)—C(=O)—O—C₄H₉ | 1.0 |
| | —O—(CH₂)₈—O—⟨○⟩—(N=N, S)—C₇H₁₅ | 0.5 |
| | —O—(CH₂)₁₁—O—⟨○⟩—(N=N, S)—C₇H₁₅ | 0.5 |
| | $S_A$ 138 I | |

| | | | |
|---|---|---|---|
| 83 | 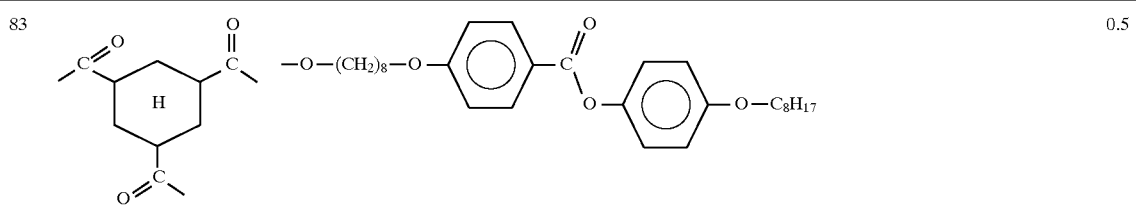 | | 0.5 |
| | | 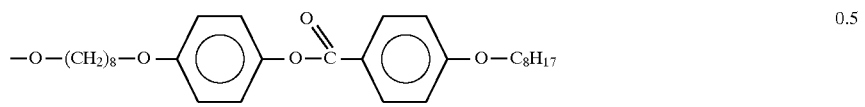 | 0.5 |
| | | 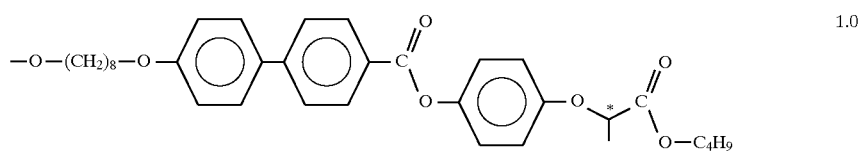 | 1.0 |
| | | 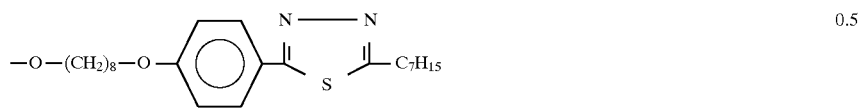 | 0.5 |
| | | 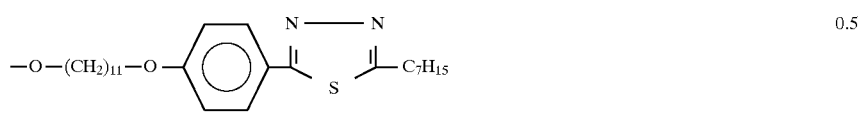 | 0.5 |
$S_A$ 103 I
| | | | |
|---|---|---|---|
| 84 | 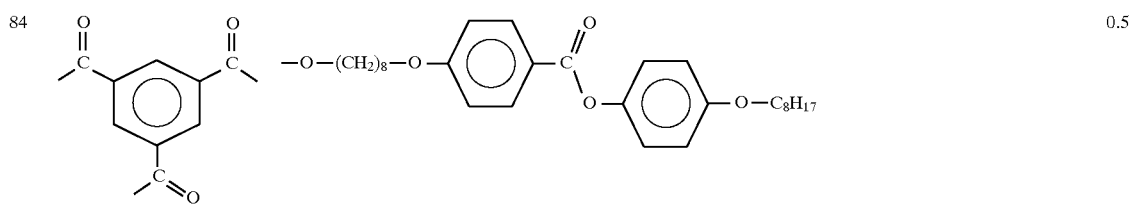 | | 0.5 |
| | | 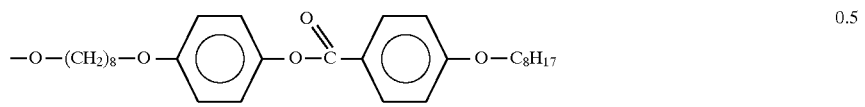 | 0.5 |
| | | 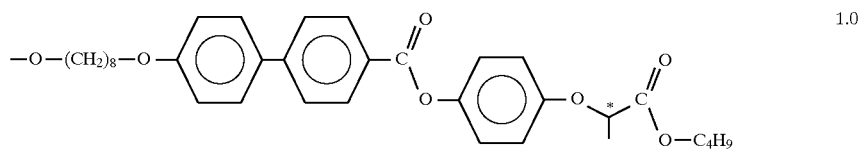 | 1.0 |
| | | 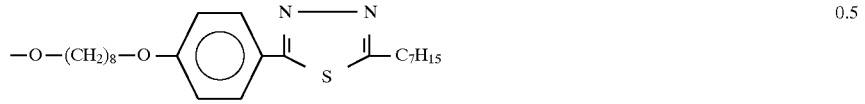 | 0.5 |
| | | 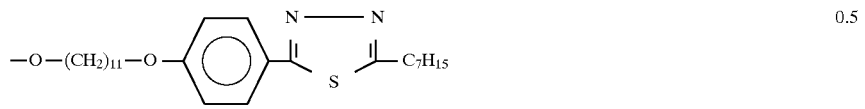 | 0.5 |
$S_A$ 105 I

| | | |
|---|---|---|
| 85 | 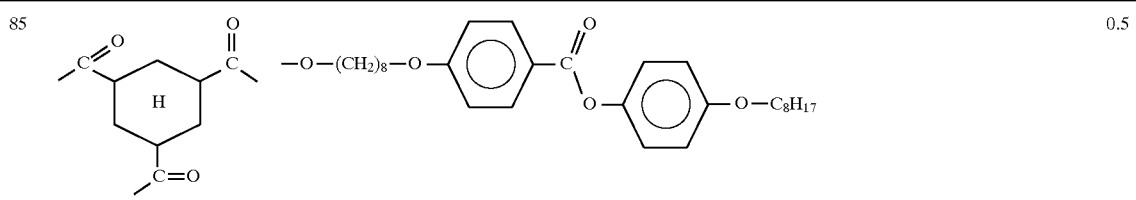 | 0.5 |
| | 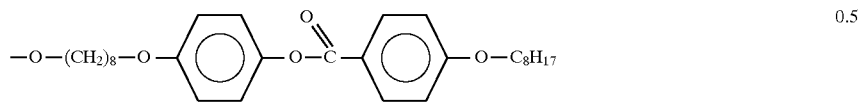 | 0.5 |
| | 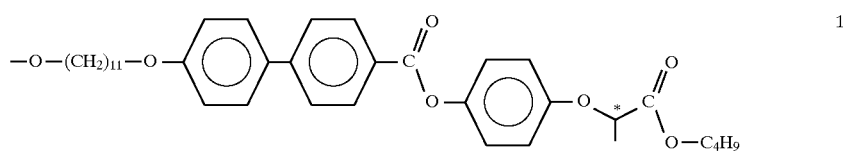 | 1 |
| | 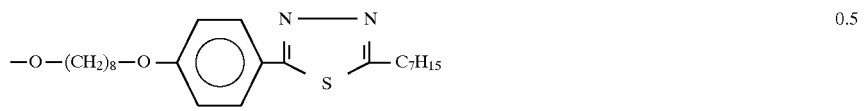 | 0.5 |
| | 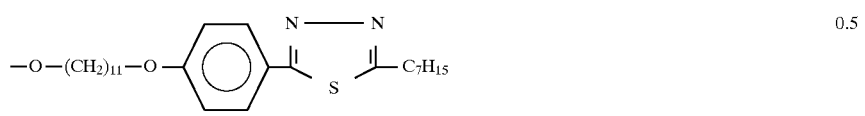 | 0.5 |
$S_x$ 42 $S_c$* 65 $S_A$ 104 I
Θ (40° C.): 21°
$P_s$ (40° C.): 50 $nC/cm^2$
| | | |
|---|---|---|
| 86 | 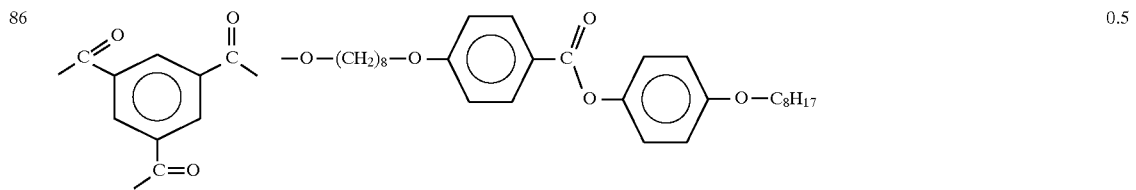 | 0.5 |
| | 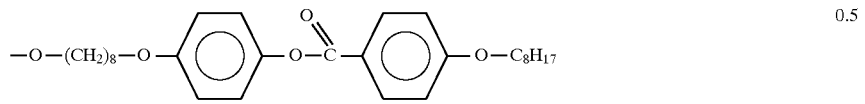 | 0.5 |
| | 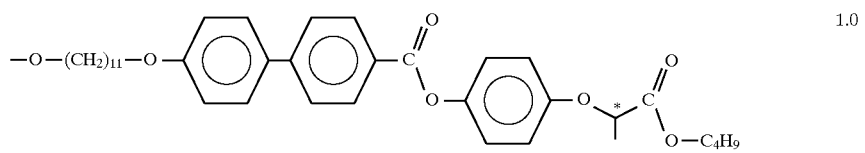 | 1.0 |
| | 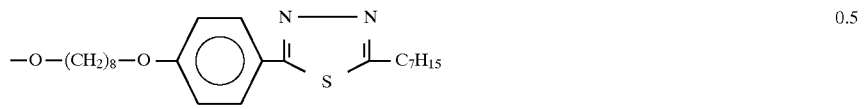 | 0.5 |
| | 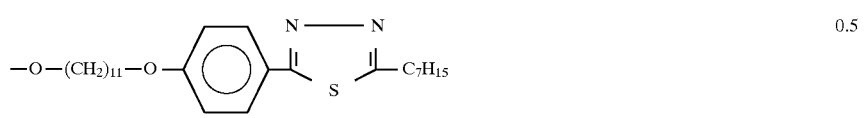 | 0.5 |
$S_c$ 96 $S_A$ 105 I -continued
87 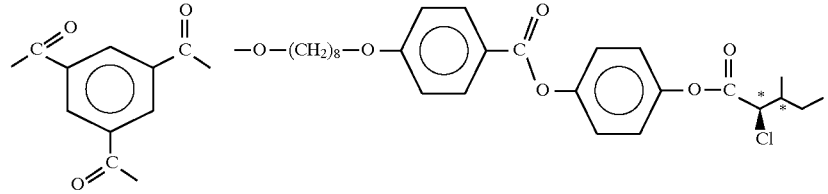
$S_c$ 47 I
88 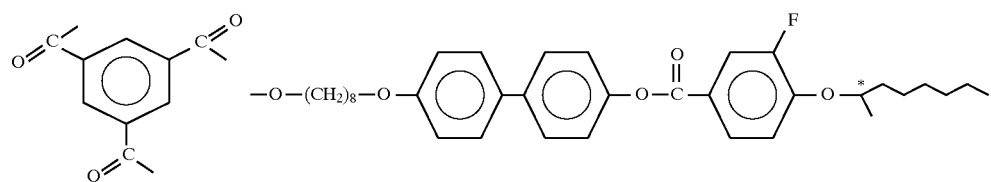
$S_x$ 82 $S_c$ 121 $S_A$ 160 I
89 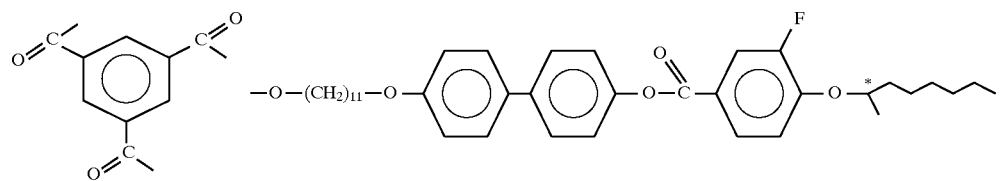
$S_x$ 85 $S_c$ 117 $S_A$ 124 I
90 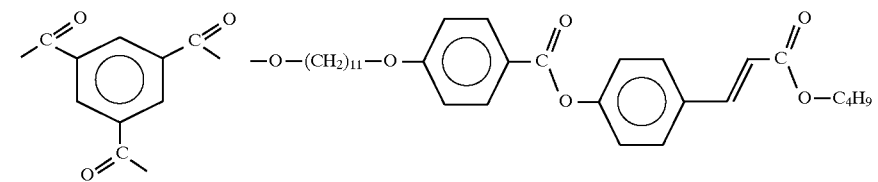
$S_c$ 45 $S_A$ 101 I
91 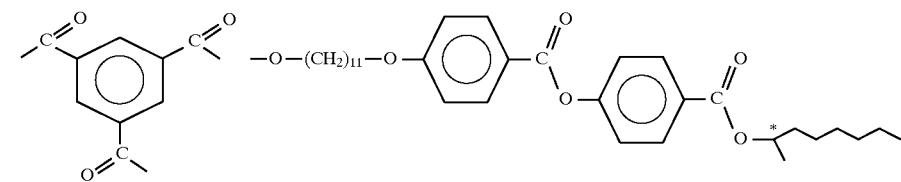 1.5
 0.75
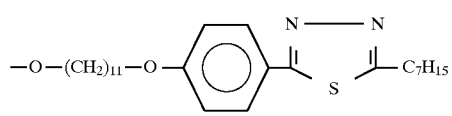 0.75
$S_x$ 40 $S_c$ 53 $S_A$ 68 I
Θ (44° C.): 22°
$P_s$ (44° C.): 35 nC/cm$^2$
92 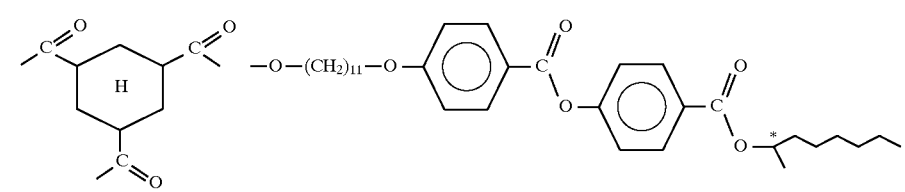 1.5

-continued

—O—(CH$_2$)$_8$—O—[phenyl]—C(=S)—N=N—C$_7$H$_{15}$    0.75

—O—(CH$_2$)$_{11}$—O—[phenyl]—C(=S)—N=N—C$_7$H$_{15}$    0.75

S$_c$ 71 I
Θ (30° C.): 26°
P$_s$ (25° C.): 80 nC/cm$^2$

We claim:
1. A liquid-crystalline compound of the formula I

$$X(—Y—A—Y—M—Y—B)_3 \quad I,$$

where
- X is trisubstituted cyclohexyl wherein the (—Y—A—Y—M—Y—B) substituents are in the meta-position with respect to one another,
- each Y, independently of the others, is a direct bond, —COO—, —OCO—, —O—, —COHN— or —CON(R)—, where R is C$_1$- to C$_4$-alkyl,
- A is a spacer,
- B is a C$_2$- to C$_{30}$-alkyl or -alkenyl, where the radicals may be linear or branched, may be interrupted once or more than once by O, OCO, COO, $$\underset{O}{CH\text{—}CH},$$

NH or N(CH$_3$), and may be substituted by phenyl, fluorine, chlorine, bromine, cyano or hydroxyl, and
- M is a mesogenic group of the formula $$(T—Y^1)_r—T,$$

where
- each T, independently of the others, is an aromatic or heteroaromatic radical,
- each Y$^1$, independently of the others, is O, COO, OCO, CH$_2$O, OCH$_2$ or a direct bond, and
- r is from 1 to 3.

2. A liquid-crystalline compound of the formula I as claimed in claim 1, where Y is O, COO or OCO.

3. A liquid-crystalline compound of the formula I as claimed in claim 1, containing spacers having 2 to 12 carbon atoms.

4. A liquid-crystalline compound of the formula I as claimed in claim 1, where B is C$_2$- to C$_{11}$-alkyl or -alkenyl which may be interrupted by O, OCO, COO, $$\underset{O}{CH\text{—}CH},$$

NH or N(CH$_3$) and may be substituted by phenyl, fluorine, chlorine, bromine, cyano or hydroxyl.

5. A liquid crystalline compound as claimed in claim 4, where Y$^1$ is COO, OCO or a direct bond.

6. A liquid-crystalline compound as claimed in claim 5, where B is C$_3$- to C$_{11}$-alkyl which is bonded via O, COO or OCO, may be interrupted once or more than once by O.

7. A liquid-crystalline compound as claimed in claim 5, where B is chiral C$_3$- to C$_{11}$-alkyl which is bonded via O, COO or OCO, may be substituted by fluorine, chlorine, bromine, cyano or hydroxyl and may be interrupted by O, COO, OCO or $$\underset{O}{CH\text{—}CH}.$$

8. A liquid-crystalline compound as claimed in claim 7, where B is chiral C$_3$- to C$_{11}$-alkyl which is bonded via O, COO or OCO, may be substituted by fluorine, chlorine, bromine or hydroxyl and may be interrupted by O or COO.

9. A liquid-crystalline compound as claimed in claim 6, wherein said C$_3$- to C$_{11}$- alkyl is unbranched.

10. A mixture, comprising the liquid-crystalline compound as claimed in claim 1 and a second different liquid crystal compound.

11. The liquid-crystalline compound of formula I as claimed in claim 1, wherein A is selected from the group consisting of (CH$_2$)p, (CH$_2$CH$_2$O)$_m$CH$_2$CH$_2$, CH$_2$CH$_2$SCH$_2$CH$_2$, CH$_2$CH$_2$NHCH$_2$CH$_2$, $$\underset{\underset{CH_2CH_2N—CH_2CH_2,}{|}}{CH_3} \quad \underset{\underset{(CH_2CHO)_mCH_2CH}{|}}{CH_3} ,$$

$$\underset{\underset{(CH_2)_6CH}{|}}{CH_3} \text{ and } \underset{\underset{CH_2CH_2CH}{|}}{Cl}$$

where
m is from 1 to 3 and
p is from 1 to 12.

* * * * *